United States Patent [19]

Chang et al.

[11] Patent Number: 5,200,323
[45] Date of Patent: Apr. 6, 1993

[54] IN VITRO METHOD TO DETERMINE THE SAFETY OF MODIFIED HEMOGLOBIN BLOOD SUBSTITUTES FOR HUMAN PRIOR TO CLINICAL USE

[75] Inventors: Thomas M. S. Chang, St-Lambert; Colin Lister, Brossard, both of Canada

[73] Assignee: McGill University, Montreal, Canada

[21] Appl. No.: 828,680

[22] Filed: Jan. 31, 1992

[51] Int. Cl.$^5$ ............................................. C12Q 1/34
[52] U.S. Cl. .......................................... 435/18; 435/4; 435/7.1; 436/66; 436/821
[58] Field of Search ................. 435/4, 18, 7.1; 436/66, 436/821

[56] References Cited

PUBLICATIONS

Winslow-Hemoglobin-based Red Cell Substitutes-John Hopkins University Press-pp. 199-201.
Chang-Biomaterials, Artificial Cells and Immobilization Biotechnology-vol. 19 No. 2 (1991) pp. 303 & 422.
Fratantone-Transfusion vol. 31 No. 4 (1991) pp. 369-371.
Feola et al.-Chem. Abst. vol. 109 (1988) pp. 122, 233t.

*Primary Examiner*—Sam Rosen
*Attorney, Agent, or Firm*—Fitzpatrick, Cella, Harper & Scinto

[57] ABSTRACT

The present invention relates to an in vitro method to determine the safety of modified hemoglobin blood substitutes for human subjects prior to their clinical usages, wherein the method is based on complement activation reaction from adding modified hemoglobin blood substitutes to a human plasma sample and comprises the steps of: a) obtaining at least one plasma sample from at least one human subject by i) taking a blood sample and immediately centrifugating; and ii) separating the centrifuged blood sample of step i) and retaining the supernatant plasma; b) mixing the plasma of step ii) with the modified hemoglobin blood substitutes or control-ringer in a weight/volume ratio of about 4:1; c) incubating for a time sufficient to allow for a complement activation reaction to occur; d) adding the product of step c) to an appropriate volume of saline in an EDTA tube; and e) analyzing the degree of complement activation by analysis of the product of step d); thereby determining the safety of the modified hemoglobin blood substitutes relative to the human subject plasma sample based on the detection of complement activation.

19 Claims, 1 Drawing Sheet

IN VITRO METHOD TO DETERMINE THE SAFETY OF MODIFIED HEMOGLOBIN BLOOD SUBSTITUTES FOR HUMAN PRIOR TO CLINICAL USE

BACKGROUND OF THE INVENTION

Blood is a living tissue; transfusion of it or of its cellular components from a donor to a recipient is a form of transplantation. About 11 to 12 million transfusions are given yearly in the United States, and the number is steadily increasing. The decision to transfuse is a clinical judgment that requires weighing the possible benefits and known hazards with alternative treatments. A transfusion not specifically indicated is contraindicated.

In the United States, regulations for collecting storing, and transporting blood and its components are established by the Federal Drug Agency (FDA), and sometimes also by state or local health authorities. The American National Red Cross and American Association of Blood Banks also have standards affecting their respective systems. Screening a donor includes a health interview, testing for Hemoglobin (Hb), and taking the temperature, pulse rate, and blood pressure (BP).

Before use, blood must be classified for suitability. This includes ABO and Rh typing, antibody screening, STS, a test for hepatitis B surface antigen (HBsAg), and tests to detect antibodies to the virus that causes acquired immunodeficiency syndrome (AIDS). The container label and the federally required Circular of Information give the results of these tests and important information and cautions and should be consulted by physicians using blood transfusions.

The various components of blood can be separated, concentrated, and stored individually for precise replacement of patient needs.

Red blood cells (RBCs) are transfused to replace Hb or $O_2$ carrying capacity, including blood lost at surgery, and to prime extracorporeal circuits. When volume expansion is required, other fluids can be used concurrently or separately.

Frozen-thawed RBCs are costly and mainly used for patients who have multiple blood group antibodies or antibodies to high frequency antigens.

Wasted RBCs (by continuous-flow washing) are free of almost all traces of plasma and of most white blood cells (WBCs) and platelets. They are suitable for patients who have severe reactions to plasma (eg, severe allergies or IgA immunization), or for those who have leucocyte antibodies and repeated febrile transfusion reactions.

The four ABO blood types are determined by testing for the presence or absence of A and B antigens on the RBCs using Anti-A and Anti-B reagents (forward or cell typing), and by testing for Anti-A and Anti-B in the serum using A and B reagents RBCs (serum or reverse typing).

There are several reactions that accompany or follow intravenous administration of blood or blood components.

Hemolytic Reactions

Hemolysis can result from blood group incompatibility, incompatible plasma or serum, hemolyzed or fragile RBCs. Incompatibility is the most frequent cause of hemolysis despite advances in blood typing and testing.

Febrile Reactions

Reactions consisting of chills, fever with a rise of at least 1° C., and sometimes headache and back pain, rarely progressing to cyanosis and shock. In some patients, after many transfusions or pregnancies, leucocyte antibodies appear in response to antigens of transfused or fetal WBCs.

Allergic Reactions

Reactions due to hypersensitivity of the patient to an unknown component in donor blood are common, usually due to allergens in donor plasma, or, less often, to antibodies from an allergic donor.

Disease Transmission

Virus hepatitis may follow the infusion of whole blood, plasma, or other products prepared from human blood, notably AHF and factor IX concentrate.

Acquired immunodeficiency syndrome (AIDS): The causative agent of this condition has been identified as human immunodeficiency virus (HIV); epidemiologic evidence indicates that it is infectious and blood-borne. A few patients with AIDS, not belonging to any of the known high-risk groups, have a history of receiving blood products and their disease is considered "transfusion-associated".

Cytomegalovirus (CMV) can be transmitted by leucocytes in transfused blood. Usually its effects are either absent or mild, and need cause no concern.

Bacterial infection: Despite careful preparation, from 2 to 5% of all blood drawn contains a few bacteria, presumably from the donor's skin.

Malaria is transmitted easily by infected donor blood. Many donors are unaware that they have malaria, certain varieties of which may be latent and transmissible for 10 to 15 years.

Syphillis may be transmitted by fresh blood from a donor with the disease, but the incidence is very rare.

Modified Hemoglobin

Red blood cell contains hemoglobin which carries oxygen to tissues as required. Red blood cell is the best transfusion material at present. However, as described above, it does present a number of problems. In particular, donor blood can be in short supply, especially in major disaster situation or during war. Red blood cell transfusions also require crossmatching. They have a very short storage time, unless they are stored by some expensive and complex means. During the last few years, the potential problem of the AIDS transmission through blood transfusion has evolved.

As a result, a number of centres have investigated the potential uses of hemoglobin extracted from red blood cells. Extracted hemoglobins which are transfused to a patient are rapidly removed from the patient circulating blood; they do not carry and release oxygen efficiently and they can be toxic. Unfortunately, hemoglobin cannot be used as such for transfusion. Because of these reasons, hemoglobin have to be modified before it can be used as a blood product.

Presently, there are two major groups of modified hemoglobin; 1) the encapsulated hemoglobin and 2) the crosslinked hemoglobin (PROC. 1983 2nd INTL. SYMP. BLOOD SUBS., San Francisco, R. P. Geyer and G. J. Nemo, Alan R. Liss Inc. Publisher, New York, pp. 1–468; PROC. 1987 3rd INTL. SYMP. BLOOD SUBS., T. M. S. Chang and R. P. Geyer, 1988, Marcel Dekker Publisher, USA, pp. 1-708; PROC. 1989, SYMP. BLOOD SUB. BIOMAT., ART. CELLS AND ART. ORGANS, R. Winslow and T. M. S. Chang, 1990, vol. 18, pp. 133-366; ABSTRACTS 1991 4th INTL. SYMP. BLOOD SUBS. BIOMAT., ART. CELLS AND IMMOBI. BIOTECH., T. M. S. Chang and R. P. Geyer, 1991, vol. 19, pp. 299-520). Crosslinked hemoglobin is subdivided into polyhemoglobin, conjugated hemoglobin and intramolecular crosslinked hemoglobin.

Animal studies carried out in many centres showed that these modified hemoglobin are effective in animal for resuscitating animals which would have otherwise died from severe bleeding. Other areas of applications for red blood cell blood substitutes were also demonstrated. The first preliminary clinical trial in a very small number of patients was approved by the FDA and completed in the United States in 1989. Preliminary report appears to be safe. However, in March of 1990, the FDA called a meeting to announce that there are observed unexplained intense and severe reactions in clinical trials carried out.

Animal Safety Studies not Valid for Human

This is surprising since animal studies carried out by many groups showed that modified hemoglobins are safe and without adverse effects. The animal result does not compare to human study. Reactions in human are different to animal reactions, especially in immunological type of reactions including anaphylactic reactions, antigen-antibody reactions, allergic reactions.

In other words if a product is immunologically safe in animals, it is not necessarily safe in humans. There is an urgent need to fill the gap between animals study and phase I clinical trial in human patients. A preclinical screening test for modified hemoglobin, after its safety has been demonstrated in animals, is needed before it can be tested in patients. Furthermore, screening of industrial production batches is needed. There are variations from person to person in human immunological reactions.

The infusion of large amount of modified hemoglobin as blood substitute can potentially result in hypersensitivity and anaphylactic reactions, antibody-antigen reactions and other. Therefore, very careful efficacy and safety animal studies of modified hemoglobin blood substitute are required before phase I of the clinical trial is started. However, one major problem is to select the right type of animals for testing before clinical trial, since one need to be sure that response in human will be the same as in the test animals.

Another important area which is being developed is non-human sources of hemoglobin. Human hemoglobin is theoretically the most optimal source because there is not as much immunological problems as with red blood cells transfusion, but human hemoglobin could be in short supply because it has to come from donor blood. There is considerable recent researches conducted to determine whether bovine hemoglobin can be used to prepare modified hemoglobin. Extensive development is also conducted on recombinant human hemoglobin from microorganisms and even animals. The importance of an in vitro human preclinical screening test will increase considerably if these types of hemoglobin are used to prepare modified hemoglobin for human use, since the result of animal safety studies is not necessary the same as human.

Furthermore, even if a given hemoglobin blood substitute product is without adverse side effects in a small number of phase I clinical trial patients, there may still be some patients who may be more sensitive to this hemoglobin product. Presently, there exists no screening test to detect patients with potential severe hypersensitivity to hemoglobin products in large scale clinical trials and later on in routine clinical applications.

In Vitro Screening Test Specific for Human Response

It would be highly desirable to be provided with an in vitro screening test which would be based on using human blood or plasma to determine the safety of modified hemoglobin blood substitutes for human prior to clinical use. This type of test would provide a bridge between the animal testing and the human clinical trial of modified hemoglobin blood substitutes.

Further, it would be highly desirable to be provided with an in vitro screening test so specific that one could determine the safety of modified hemoglobin blood substitutes for a particular patient, who is to receive the blood substitutes, prior to his actual clinical use of the blood substitutes.

Finally, it would be highly desirable to be provided with an in vitro screening test for screening industrial productions of modified hemoglobin blood substitutes to rule out potential problems before starting the clinical trial of the blood substitute by a population of patients or human subjects.

SUMMARY OF THE INVENTION

Surprisingly and in accordance with the present invention, there is provided an in vitro method to determine the safety of modified hemoglobin blood substitutes for human before their clinical trial in human. The in vitro method of the present invention is based on the effect of modified hemoglobin blood substitute on complement activation when added to human plasma.

The present invention relates to an in vitro method to determine the safety of modified hemoglobin blood substitutes for human subjects prior to their clinical usages, wherein the method is based on complement activation reaction from adding modified hemoglobin blood substitutes to a human plasma sample and includes the steps of: a) obtaining at least one plasma sample from at least one human subject by: i) taking a blood sample and immediately centrifuging; and ii) separating the centrifuged blood sample of step i) and retaining the supernatant plasma; b) mixing plasma of step ii) with the modified hemoglobin blood substitutes or the control-ringer in a weight/volume ratio of about 4:1; c) incubating for a time sufficient to allow for a complement activation reaction to occur; d) adding the product of step c) to an appropriate volume of saline in an EDTA tube; and e) analyzing the degree of complement activation by analysis of the product of step d); thereby determining the safety of the modified hemoglobin blood substitutes relative to the human subject plasma sample based on the detection of complement activation.

In accordance with the present invention, there is provided an in vitro screening method which is based on using human blood or plasma to determine the safety of modified hemoglobin blood substitutes for human prior to clinical use. This method provides a bridge between the animal testing and the human clinical trial of modified hemoglobin blood substitutes.

In accordance with the present invention, there is provided an in vitro screening method so specific that one can determine the safety of modified hemoglobin blood substitutes for a particular patient, who is to receive the blood substitutes, prior to his actual clinical use of the blood substitutes.

In accordance with the present invention, there is provided an in vitro method for screening industrial productions of modified hemoglobin blood substitutes to follow: (1) the different steps of industrial production, (2) different batches produced and (3) screening before the packaging the final product for human use.

The in vitro method of the present invention can also be used for human preclinical trial studies and for screening before human clinical use of modified hemoglobin blood substitutes.

Most of the problems related to potential hypersensitivity reactions, anaphylactic reactions, effects due to antibody-antigen complexes, and others could be detected in vitro by the method of the present invention.

Other advantages of the present invention will be readily illustrated by referring to the following description.

DETAILED DESCRIPTION OF THE INVENTION

Figure 1:
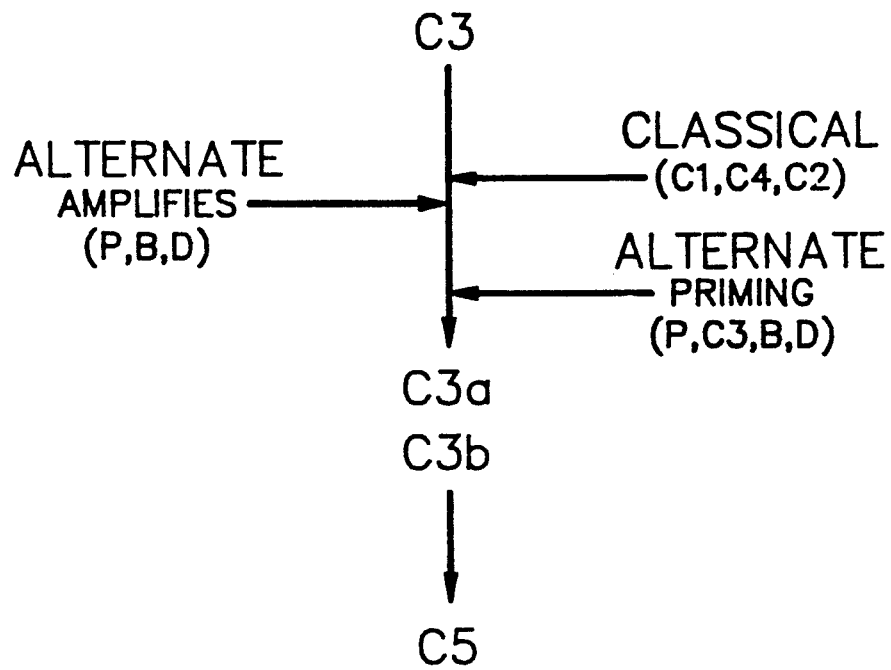
FIG. 1 is diagram scheme of the complement activation pathway.

The best in vitro test before clinical trial in human is the method of the present invention which uses the human plasma. The in vitro method of the present invention is based o the degree of complement activation of human plasma upon the addition of the modified hemoglobin blood substitutes.

In the preclinical test provided by the method of the present invention, a plasma sample is obtained from a human subject and modified hemoglobin is added to the plasma sample. Then, the sample may be analyzed for $C3a$ level to analyze possible C3 complement activation. Using the method of the present invention, one can test the hemoglobin product to determine if it causes any complement activation in human plasma; it is the next closest test to actual injection into human.

Trace amount of blood cell membrane material may be present during the extraction of hemoglobin from red blood cells, and it can be incorporated into the modified hemoglobin preparation. This trace amount of blood cell membrane material may not be detectable using the animal testing procedure, whereas upon infusion into a patient it can cause adverse reactions, including complement activation.

The method of the present invention can also test for different types of antibody-antigen complexes. It can also test for the contamination of the modified hemoglobin preparation including endotoxin, trace fragments of microorganisms. It can also detect contaminants resulted from large scale production of modified hemoglobin, including chemicals, trace amount of some polymers which can cause complement activation, emulsifying agents and some types of organic solvents.

The most important feature of the method of the present invention is that before clinical testing in patients, one can take plasma from each individual potential participant in clinical trial and test their plasma with modified hemoglobin used for clinical trial and therefore, foresee the reactions of each individual person. Thereafter, before clinical trial is initiated, one already knows which patient would have reaction and hence would not subject the patient to the test The in vitro method of the present invention involves collecting heparinised blood sample, centrifuging the collected blood sample, separating the centrifuged blood sample and retaining the supernatant plasma. The blood sample may be taken from a given subject or a given population of subjects. The blood sample collected may contains 10IU of heparin/ml of blood and may be centrifuged at a range of about 3000 to 5500 g and at about 0° to 4° C. for about 15 to 30 minutes; and is preferably centrifuged at 5500 g and 2° C. for 20 minutes.

It is possible to either proceed with the subsequent steps of the method of the present invention or to freeze the heparinised plasma at about −30° to −70° C. until use, preferably at −70° C.

Then, it is followed by mixing the plasma with the modified hemoglobin blood substitutes or the control-ringer in a weight/volume ratio of about 4:1, which could be 400 lambda of the plasma and 100 lambda of modified hemoglobin blood substitutes samples.

Then, the mixture is incubated for a time sufficient to allow for a complement activation reaction to occur, which preferably consists in incubating in a shaker at about 5 to 100 rpm and about 20° to 37° C. for about 15 minutes to 3 hours; and more preferably incubating in a shaker at 60 rpm and 37° C. for 1 hour.

The incubated product is added to an appropriate volume of saline in an EDTA tube to stop the reaction, preferably about 0.5 to 3 ml of saline, more preferably 1.6 ml of saline.

It is possible to either proceed with the subsequent steps of the method of the present invention or to freeze the heparinised plasma at about −30° to −70° C. until use, preferably at −70° C.

Then, it is followed by determining the degree of complement activation by analysis of the incubated product. The complement activation analysis is conducted by measuring the level of at least one member of the group consisting of C3, C4, $C3a$, $C3b$, $C3c$ and C5 using a standard technique, preferably measuring $C3a$ by radioimmunoassay; whereby the safety of the modified hemoglobin blood substitutes relative to the human subject plasma sample is determined.

FIG. 1 shows the complement activation pathway. In order to determine the degree of conversion of C3 into $C3a$, one can measure the change in the level of C3, C4, $C3a$, $C3b$, $C3c$ and C5. The more conversion of C3 to $C3a$, the more unsafe is the blood substitute product from the human plasma sample taken.

The method of the present invention, based on the complement activation analysis allows the screening of levels, at least sufficient to cause complement activation in human subjects, of endotoxin, cell membrane material, organic solvents, polymers and of chemical emulsifiers present in the modified hemoglobin blood substitutes.

The method of the present invention can be used for testing industrial batches of modified hemoglobin blood substitutes which comprises using a plasma sample or pool of plasma samples from human subjects.

The method of the present invention may be used for the screening of large populations of patients before clinical trial or usage.

There are different potential factors in hemoglobin preparations which can cause complement activation. These most likely include endotoxins and cell membrane materials such as some types of phospholipids or membrane antigens. Chemicals such as surfactants and organic solvents can also increase complement activation. This further shows the need for an overall screening test as a step before the actual use of hemoglobin preparations in human. The method of the present invention can avoid potential clinical problems not detected by animal safety studies or by more specific tests for specific substances. The in vitro method of the present invention is useful in this regard.

A similar test has been used sometimes for screening gamma-globulin production for human use. However, this test is based on complete complement hemolytic activity (CH50) in guinea pig serum. Guinea pig serum, though very sensitive to complement activation, may not reflect the same type of response as in human.

The in vitro method of the present invention of using human plasma gives a closer response to that of human. It is especially useful when the plasma of the same patient who is to receive the hemoglobin preparation can be used for screening. This allows for a very specific screening test of the specific patient to the exact specific modified hemoglobin preparation.

The present invention will be more readily understood by referring to the following examples which are given to illustrate the invention rather than to limit its scope.

EXAMPLE I

Measurement of C3a to Determine the Safety of a Modified Hemoglobin Blood Substitute Sample Blood is obtained by clean venous puncture from human volunteers into 50 ml polypropylene (Sastedt) heparinised tubes (10 IU heparin/ml of blood). The plasma is immediately separated by centrifugation at 5500 g at 2° C. for 20 minutes, the plasma is decanted and frozen in separate portions at −70° C. Serum is not used because coagulation initiates complement activation. EDTA is not used as an anticoagulant, because it interferes with complement activation reactions.

Hemoglobin Solutions

For this example, two (2) hemoglobin solutions are used; solutions A and B. Solution A does not cause significant complement activation. Solution B causes complement activation. Solutions A and B are used in the following mixtures for testing (1) A 100%; (2) A 75% +B 25%; (3) A 50%+B 50%; (4) 25%+B 75%; (5) B 100%.

Effects of Hemoglobin Solutions on Human Plasma

Immediately before use, the plasma sample is thawed. 400 lambda of the plasma is pipetted into 4 ml sterile polypropylene tubes (Fischer). 100 lambda of pyrogen free saline (or Ringer Lactate) for injection is added to the 400 lambda of human plasma as control. 100 lambda of one of the test solutions including hemoglobin or modified hemoglobin is added to one of the other tubes containing 400 lambda of human plasma.

The reaction mixtures are incubated at 37° C. at 60 rpm for 1 hour in a Lab-Line Orbit Environ Shaker ™ (Fisher Scientific, Montreal, Canada). After 1 hour the reaction is stopped by adding 0.4 ml of the reaction mixture to 1.6 ml of sterile saline in a 2 ml EDTA sterile tube (Becton Dickenson). The samples are immediately stored at −70° C. until analyzed.

The base line control level of complement activation will vary with source of human plasma and how it is obtained. Therefore a control base line level must be used for each analysis. Furthermore, all control and test studies should be carried out in triplicate.

Complement Activation Analysis: C3a measurement

The analytical kit for human complement activation designed for C3a qualitative measurements is purchased from Amersham Canada. The method of analysis is the same as that of the instructions in the kit with 2 minor modifications. Centrifugation is carried out at 10,000 g for 20 minutes. After the final step of inversion, the inside wall of the tubes is carefully blotted with Q-tips.

Endotoxin Measurement

Endotoxin measurements are based on the Limulus Amebocyte Lysate "PYROTELL" Test (Catalogue 100-5 ™) (Associates of Cape Cod, Woods Hole, Mass, USA) with a sensitivity of 0.03 EU/ml. For hemoglobin, this or other tests which are not based on colour changes can be used.

Measured Complement Activation after Addition of Hemoglobin

Figure 2:
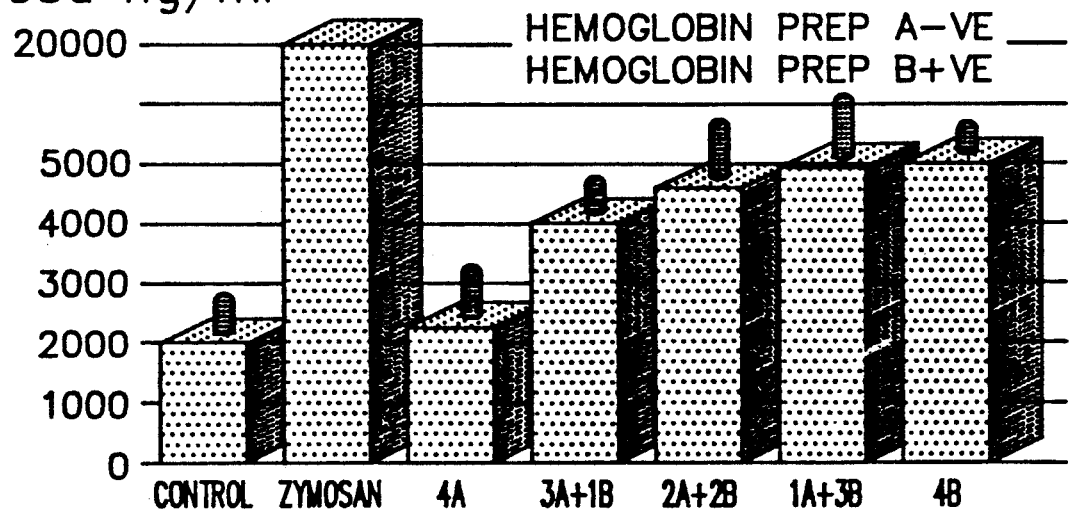
FIG. 2 is a graph of the results of Table 1 below.

Using the method of the present invention as described herein, the measured C3a levels (ng/ml) in plasma are: control, 1,980±280; Zymosan, 20,000; Hemoglobin preparation A, 2,227±617; Hemoglobin preparation B, 4,967±153; A 75%+B 25%, 3,967±270; A 50%+B 50%, 4,553±517; A 25%+B 75%, 4,920±430. The results obtained are summarized in Table 1 and illustrated in FIG. 2.

TABLE 1

| HEMOGLOBIN AND COMPLEMENT ACTIVATION (C3a) | |
|---|---|
| Test solution | C3a ng/ml (mean + S.D.) |
| Control | 1,980 ± 280 |
| Zymosan | >20,000 |
| A 100% | 2,227 ± 617 |
| A 75% + B 25% | 3,967 ± 270 |
| A 50% + B 50% | 4,553 ± 517 |
| A 25% + B 75% | 4,920 ± 430 |
| B 100% | 4,967 ± 153 |

Hemoglobin preparation A does not cause significant increases in C3a complement activation. Hemoglobin preparation B causes significant increase in C3a complement activation. Serial dilution of Hemoglobin preparation B in Hemoglobin preparation A continue to cause the same degree of C3a complement activation. This is not due to C3 exhaustion because Zymosan resulted in C3a of greater than 20,000 ng/ml. This demonstrates that the in vitro method of the present invention can detect complement activation even at low concentrations of the hemoglobin preparation. Factors which cause complement activation may include endotoxin, toluene extractable factors like lipids, and organic solvents.

Effects of Hemoglobin Preparations on Complement Activation in Human Plasma

Manipulation of human plasma during collection, freezing, thawing, and procedures of the screening test were enough to result in some C3a complement activation. Using the procedure described above, a control level of 1,980±280 ng/ml is obtained. This emphasizes the importance of a simultaneous control sample. After addition of hemoglobin preparation A to human plasma the C3a concentration is 2,227±617 ng/ml. This is not significantly different from control C3a level of 1,980±280 ng/ml, when control Ringer Lactate solution (pyrogen free solution for injection) is added to human plasma. Hemoglobin solution B on the other hand, when added to human plasma, results in significant increase in C3a level to 4,967±153 ng/ml. Diluting solution B with solution A (A 25%±B 75%; A 50%±B 50%; and A 75%±B 25%) still results in the same degree of C3a complement activation. At a dilution of A 75%+B 25% the C3a complement activation though significantly lowered, is still nearly as much as those for the higher concentrations. Thus, the degree of complement activation is not quantitatively proportional to the relative concentration of B and A. This is not because of the exhaustion of C3, since Zymosan when added to human plasma resulted in C3a level of 20,000 ng/ml. Thus, in vitro the method of the present invention is sensitive enough to detect the factor or factors responsible for complement activation even at much lower concentration.

EXAMPLE II

Effects of Endotoxin on Complement Activation in Human Plasma

It has been demonstrated that endotoxin in saline when added to human plasma at concentrations of as low as 0.50 EU/ml causes significant increases in C3a complement activation as measured by the above procedure. Modified hemoglobin with significant endotoxin levels also increases C3a level in the above screening test. Thus it is likely that endotoxin is one of the possible factors responsible for complement activation in human plasma.

However, endotoxin is only one of the many factors in hemoglobin preparation which can cause complement activation. For example, hemoglobin solutions which contain insufficient endotoxin by itself to cause complement activation are tested. Nevertheless, although some of these do not cause significant C3a complement activation, some other still increase C3a complement activation when added to human plasma. Therefore, the question arises as to whether (1) hemoglobin at high concentration interferes with the measurements of endotoxin in hemoglobin preparations; (2) in addition to endotoxin, there are other factors in the hemoglobin preparations which cause complement activation. The following studies are carried out.

Effects of Hemoglobin on Endotoxin Measurements

Different concentrations of endotoxin are measured in pyrogen free saline. Then the same concentrations of endotoxin are added to 10 g/dl hemoglobin solution which already contains 0.48 EU/ml of endotoxin. The results are summarized in Table 2.

TABLE 2

| Solutions | Amount present (EU/ml) | Measured amount (EU/ml) |
|---|---|---|
| Control saline | 0 | 0 |
| Saline (0.25 EU/ml) | 0.25 | 0.25 |
| Saline (0.50 EU/ml) | 0.50 | 0.50 |
| Saline (1.00 EU/ml) | 1.00 | 1.00 |
| Hemoglobin (0.48 EU/ml) | 0.48 | 0.48 |
| Hemoglobin (0.725 EU/ml) | 0.725 | 0.725 |
| Hemoglobin (0.980 EU/ml) | 0.980 | 0.970 |
| Hemoglobin (1.48 EU/ml) | 1.480 | 1.460 |

The above assay shows that hemoglobin does not interfere with endotoxin measurements based on the LAL "PYROTELL" Test.

Effects of Endotoxin "Free" Toluene Extracted Hemoglobin on C3a Complement Activation in Human Plasma The above results show that high concentrations of hemoglobin does not interfere with the measurement of endotoxin in hemoglobin preparations (Table 2). This means that in the endotoxin "free" hemoglobin preparations discussed earlier, complement activation must be due to another factor or factors. Thus, in addition to endotoxin, there could be at least another factor. For instance, hemoglobin solution prepared by hemolysis followed only by centrifugation caused C3a complement activation when added to human plasma.

After toluene extraction and crystallisation, the resulting hemoglobin solution no longer causes C3a complement activation. Toluene lipid extracted stroma-free hemoglobin with endotoxin level of less than 0.24 EU/ml when added to human plasma does not cause a significant increase in C3a. Endotoxin level of less than 0.24 EU/ml is the approved U.S.P. level for intravenous infusion fluids. Modified hemoglobin prepared from this lipid extracted hemoglobin solution does not result in significant increase in C3a level when added to human plasma.

While the invention has been described in connection with specific embodiments thereof, it will be understood that it is capable of further modification and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows from the scope of the appended claims.

We claim:
1. An in vitro method to determine the safety of modified hemoglobin blood substitutes for human subjects prior to their clinical usage, wherein said method is based on complement activation reaction from adding said modified hemoglobin blood substitutes to a human plasma sample and comprises the steps of:
   a) obtaining at least one plasma sample from at least one human subject by:
      i) taking a blood sample and immediately centrifuging; and
      ii) separating said centrifuged blood sample of step i) and retaining the supernatant plasma;
   b) mixing said plasma of step ii) with said modified hemoglobin blood substitutes or control-ringer in a weight/volume ratio of about 4:1;
   c) incubating for a time sufficient to allow for a complement activation reaction to occur;

d) adding the product of step c) to an appropriate volume of saline in an EDTA tube; and e) analyzing the degree of complement activation by analysis of the product of step d);

thereby determining the safety of said modified hemoglobin blood substitutes relative to said human subject plasma sample based on the detection of complement activation wherein an increase in complement activation being indicative of increased toxicity.

2. The method of claim 1, wherein step a) further comprises:

freezing said supernatant plasma of step a) for storage; and thawing said frozen supernatant plasma immediately prior to conducting step b).

3. The method of claim 1, which further comprises:

freezing said product of step d) for storage; and thawing said frozen product of step d) immediately prior to conducting step e).

4. The method of claim 2, which further comprises:

freezing said product of step d) for storage; and thawing said frozen product of step d) immediately prior to conducting step e).

5. The method of claim 1, wherein said blood sample of step i) contains 10 IU of heparin/ml of blood and is centrifuged at a range of about 3000 to 5500 g and at about 0° to 4° C. for about 15 to 30 minutes.

6. The method of claim 1, wherein said blood sample of step i) contains 10 IU of heparin/ml of blood and is centrifuged at 5500 g and at 2° C. for 20 minutes.

7. The method of claim 1, wherein step b) consists in mixing about 400 lambda of said plasma of step ii) and 100 lambda of the modified hemoglobin blood substitutes or control-ringer.

8. The method of claim 1, wherein step c) consists in incubating in a shaker at about 5 to 100 RPM and about 20° to 37° C. for about 15 minutes to 3 hours.

9. The method of claim 1, wherein step c) consists in incubating in a shaker at 60 RPM and 37° C. for 1 hour.

10. The method of claim 1, wherein step d) consists in adding the product of step c) to about 0.5 to 3 ml of saline.

11. The method of claim 1, wherein step d) consists in adding the product of step c) to about 1.6 ml of saline.

12. The method of claim 2, wherein said supernatant plasma is frozen at about $-30°$ to $-70°$ C.

13. The method of claim 2, wherein said supernatant plasma is frozen at $-70°$ C.

14. The method of claim 1, wherein the complement activation analysis of step e) is conducted by measuring the level of at least one member of the group consisting of C3, C4, C3$a$, C3$b$, C3$c$ and C5.

15. The method of claim 14, wherein the level of a member is measured using radioimmunoassay technique.

16. The method of claim 1, wherein the complement activation analysis allows the screening of levels, at least sufficient to cause complement activation in human subjects, of endotoxin, cell membrane material, organic solvents, polymers and of chemical emulsifiers present in the modified hemoglobin blood substitutes.

17. The method of claim 1, wherein the plasma sample is taken from a given subject or a given population of subjects.

18. The use of the method of claim 1 for testing industrial batches of modified hemoglobin blood substitutes which comprises using a plasma sample or pool of plasma samples from human subjects.

19. The use of the method of claim 1 for the screening of large population of patients before clinical trial or usage.

* * * * *